United States Patent [19]
O'Daniel, Sr.

[11] 3,989,895
[45] Nov. 2, 1976

[54] STETHOSCOPE TRANSDUCER

[76] Inventor: Philip S. O'Daniel, Sr., 1640 Ashland Ave., St. Paul, Minn. 55104

[22] Filed: May 8, 1974

[21] Appl. No.: 467,893

[52] U.S. Cl. .............................................. 179/1 ST
[51] Int. Cl.² ........................ H04R 1/46; A61B 7/04
[58] Field of Search ................... 179/1 ST; 181/131; 128/2 K

[56] References Cited
UNITED STATES PATENTS

| | | | |
|---|---|---|---|
| 2,419,471 | 4/1947 | Thibos | 179/1 ST |
| 3,052,756 | 9/1962 | Seven et al. | 179/1 ST |
| 3,182,129 | 5/1965 | Clark | 179/1 ST |
| 3,247,324 | 4/1966 | Cefaly | 179/1 ST |
| 3,396,241 | 8/1968 | Anderson et al. | 179/1 ST |
| 3,539,724 | 11/1970 | Keesee | 179/1 ST |
| 3,630,308 | 12/1971 | Ravin | 181/131 |
| 3,846,585 | 11/1974 | Slosberg | 179/1 ST |

*Primary Examiner*—Kathleen H. Claffy
*Assistant Examiner*—E. S. Matt Kemeny

[57] ABSTRACT

An improved stethoscope having a transducer attached to it for converting mechanically produced heart sound transmissions into an electrical signal without interrupting the mechanically produced sound which is transmitted simultaneously as an acoustical wave to the ears of the stethoscope operator.

9 Claims, 5 Drawing Figures

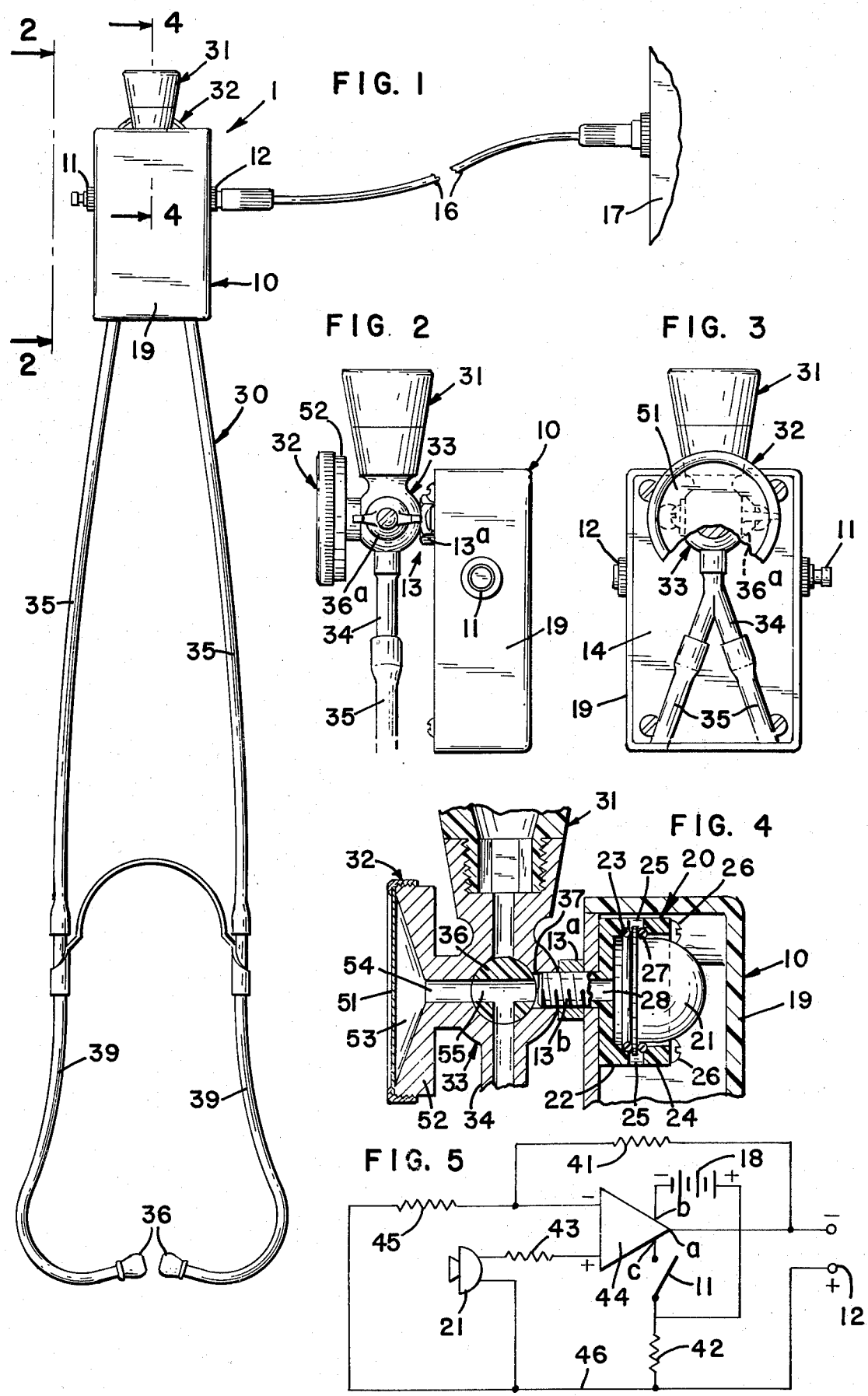

STETHOSCOPE TRANSDUCER

BACKGROUND OF THE INVENTION

1. Field of the Invention:

An electronic transducer in combination with a stethoscope for electronically monitoring the sounds which are mechanically produced by the stethoscope.

2. Description of the Prior Art:

Stethoscopes have long been used by physicians to monitor the various sounds produced by the heart. These stethoscopes typically consist of a mechanical sensor which is placed on the body of the test subject and which produce an acoustical wave in response to heart sound vibrations. The acoustical waves are transmitted through an air column contained in a flexible conduit to an earpiece inserted in the ear of the operator. As the sound wave exits the earpiece of the stethoscope, it is detected by the operator as a drumlike sound. The amplitude and frequency of the heart sounds have varying characteristics depending upon the physical condition and operation of the heart being tested. These instruments are commonly referred to as mechanical stethoscopes because they depend only upon mechanical means for the creation of the acoustical wave in response to the heart sounds.

Since mechanical stethoscopes were first developed, various attempts have been made to utilize electronic aids to enhance the monitoring of sounds which is carried out by the stethoscope. Such electronic aids have generally been used to either electronically amplify the sounds detected by the stethoscope and rebroadcast them to the stethoscope operator to aid him in his detection of heart sounds or to transmit the heart sounds as electronic signals to peripheral apparatus for such purposes as recording the heart sounds. In such devices, a microphone is typically utilized in combination with the stethoscope for picking up the acoustical wave which is transmitted through the stethoscope. The signals from the microphone are then either transmitted to the listener by means of a loudspeaker or transmitted directly to the peripheral equipment such as an oscilloscope or a recording instrument.

While these various electronic devices which have been developed for use with the stethoscope have been beneficial in that they enhance the output of the stethoscope, in each instance the electronic device has been designed such that its output is a substitution for the mechanically produced sound wave which normally is transmitted through the stethoscope to the ears of the operator. As a result, the electronic device, when in use, prevents the stethoscope user from simultaneously hearing the sound which was mechanically produced by the stethoscope. Such designs severely limit the usefulness of electronically aided stethoscopes currently available. This arises from the fact well known in the art that the sound which is "heard" by the listener when using a standard stethoscope with mechanically produced sound is different in form from electronically produced sound which is transmitted by the various electronic aids presently available. This difference in sound characteristic arises from the acoustics produced in the stethoscope when it is placed in the ears of the listener, including various reflections which are caused when the earpiece of the stethoscope is blocked off by its insertion in the listener's ear. As a result, the electrically reproduced sounds have a frequency and amplitude which is significantly different from that which is characteristically "heard" directly through the earpiece of the mechanical stethoscope. Thus, the sound "heard" by the listener through the electronic amplifying device is of a different form than that heard directly through the mechanical transmissions of the stethoscope. Because a physician or other person skilled in the use of the stethoscope becomes trained to hear certain sounds which are mechanically produced by the stethoscope, the electronically produced sounds represent a relatively foreign sound and are not accurately recognizable by the listener. For these reasons, when the electronic aid is substituted for the mechanical sound produced by the stethoscope, the stethoscope user cannot simultaneously use the stethoscope in a conventional manner to produce the mechanical sounds which are best known to the trained physician. If the person utilizing the electronically aided stethoscope for recording purposes wishes to himself listen to the heart sounds as they are produced mechanically through a stethoscope, he must either shut off the electronic aid or he must use a second stethoscope. Such operations may be very difficult because they require the handling of two pieces of equipment and both pieces of equipment cannot be placed over the exact area of the test subject body at the same time. In addition to being inconvenient, this lack of operating capacity in currently available electronic stethoscopes may produce a dangerous condition for the test subject. For example, if the heart sounds of a test subject are being electronically monitored with a presently available electronic stethoscope, the physician could not monitor the sounds himself while the electronic recording or transmitting was being accomplished. During this interval, the condition of the test subject could deteriorate considerably and perhaps dangerously.

DISCLOSURE OF PRIOR ART KNOWN TO APPLICANT

Prior to the preparation of the applicant's patent application, a patentability search was conducted which revealed the following patents that were believed to be relevant to applicant's invention.

| Patent No. | Name of Inventor | Date of Issue |
|---|---|---|
| 3,247,324 | R. Cefaly et al | April 19, 1966 |
| 1,976,707 | J. Weinstein | Oct. 9, 1934 |
| 2,849,533 | A. L. Di Mattia | Aug. 26, 1958 |
| 2,419,471 | M. F. Thibos | April 22, 1947 |
| 3,087,016 | J. D. Dahl | April 23, 1963 |
| 2,385,221 | B. Minsky | Sept. 18, 1945 |

SUMMARY OF THE INVENTION

The present invention is an electrical transducer utilized in combination with a mechanical stethoscope for converting the mechanically produced stethoscopic sounds to electrical signals. The transducer is attached to the stethoscope in such a way as to allow the stethoscope to be used for transmitting mechanically produced acoustical waves to the ears of the listener while at the same time the transducer is picking up the heart sounds produced by the stethoscope and converting them to an electrical signal for purposes of recording, rebroadcasting or other electrical reproduction.

The transducer includes a pickup microphone and an amplifying circuit for amplifying the microphone-produced signals for transmission through an output jack terminal to an associated electrical recorder or transmitter. The transducer is attached directly to the stethoscope and contains a battery power source. A momentary-contact switch is incorporated into the transducer circuitry for selective activation of the transducer by the operator of the stethoscope. Because of the design of the transducer and its method of attachment to the stethoscope, the stethoscope operator can listen to the sounds which are mechanically produced by the stethoscope at the same time he selectively actuates the transducer to produce an electrical signal to transmit the heart sound to peripheral electronic equipment.

BRIEF DESCRIPTION OF THE DRAWINGS

FIG. 1 is a top plan view of the stethoscope and attached transducer showing a cable interconnected between the transducer and a recording instrument;

FIG. 2 is a side elevational view of the apparatus of FIG. 1 along the line 2—2;

FIG. 3 is a bottom plan view of the transducer with a partial cutaway;

FIG. 4 is a detailed sectional view of the apparatus of FIG. 1 along the line 4—4;

FIG. 5 is a schematic diagram of the transducer amplification circuitry.

DESCRIPTION OF THE PREFERRED EMBODIMENT

Referring to FIGS. 1–5, wherein like numerals refer to like structural elements, a preferred embodiment of the present invention consists of a transducer equipped stethoscope 1 having a transducer 10 attached to a mechanical stethoscope 30.

In the embodiment shown in FIG. 1, stethoscope 30 is a binaural bell-type stethoscope having both a diaphragm type pickup 32 and a bell-type pickup 31, either of which may be placed against the body of the test subject to pick up heart sounds. The sounds picked up by either diaphragm pickup 32 or bell pickup 31 are transmitted through two flexible coupling conduits each designated by the numeral 35. Flexible conduits 35 each terminate in an earpiece designated by the numeral 36. When used as a simple mechanical stethoscope, the heart sounds produced by the test subject create vibrations which produce an acoustical wave in either the diaphragm pickup 32 or the bell pickup 31. This acoustical wave is transmitted through flexible conduits 35 to the earpiece 36. When the acoustical wave eminates from earpieces 36 which are placed in the operator'ears, the heart sounds are heard.

In describing the detailed structure of the transducer equipped stethoscope 1, reference should first be made to FIG. 4 which shows the detailed construction of the portion of stethoscope 30 used to pickup the heart sounds from the test subject. The embodiment of the invention shown in the FIGS. utilizes a stethoscope 30 having both a diaphragm pickup 32 and a bell pickup 31. Either can be placed against the test subject's body to receive the vibrations produced by the heart sound. Diaphragm pickup 32 consists of a diaphragm housing 52 containing an acoustical chamber 53 covered by a diaphragm 51. The heart sounds produced in the test subject create mechanical vibrations which vibrate diaphragm 51. This vibration of diaphragm 51 produces an acoustical wave in acoustical chamber 53. Acoustical chamber 53 is generally cone shaped and connects at is apex with diaphragm acoustical bore 54.

Bore 54 inturn communicates with bore 55 in selector valve 36 which will be described later. Valve bore 55 communicates with transducer 10 in a manner to be described in detail later and also to a junction element bore 56. Thus, the acoustical wave produced by the vibration of diaphragm 51 is transmitted simultaneously into the transducer 10 and into junction element bore 56.

Junction element 34 extends from valve body 33 to each of flexible conducts 35. Thus, when the acoustical wave is transmitted into bore 56, it travels through both legs of junction element 34 into each of the flexible coupling conduits 35 terminating in the earpieces 36 where it is heard by the stethoscope operator. Whether or not the transducer 10 is activated, the acoustical wave which is mechanically produced by the stethoscope can be continually heard by the operator through earpieces 36. Similarly, if the bell pickup 31 is pressed against the body of the test subject, an acoustical wave is produced in bell 34 and transmitted through bell acoustical bore 35 into valve body 33.

In the configuration shown in FIG. 4, a selector valve 36 is shown positioned in the center of valve body 33. The purpose of selector valve 36 is to allow the user of the stethoscope 1 to select either the use of diaphragm pickup 32 or bell pickup 31. In the position shown in FIG. 4, selector valve 36 allows the acoustical wave produced in diaphragm pickup 32 to be transmitted into the stethoscope. If it were desired to utilize bell pickup 31 instead of diaphragm pickup 32, selector valve 36 would be rotated 90° so that valve bore 55 is in line with bell acoustical bore 35. Then, the acoustical wave picked up by bell pickup 31 would be transmitted simultaneously through valve bore 55 into transducer 10 and into junction element bore 56 for transmission into each of flexible conduits 35 and to the earpieces 36. Selector valve 36 is operated by a wingnut 36A located on the outside of valve body 33. As in the case of diaphragm pickup 32, the acoustical wave produced by bell 31 is transmitted through earpieces 36 at all times whether transducer 10 is activated or not. This allows the user of the stethoscope 1 to utilize it continuously as a mechanical stethoscope whether the transducer 10 is utilized or not. This is beneficial in that the user of the stethoscope can continually monitor the test subject while various changes are made in the location of the stethoscope on the test subject or while recordings are made from the transducer 10 when it is activated. In addition to being used for continuous monitoring of the mechanically produced sounds through earpieces 36, stethoscope 1 is equipped with separate means for converting the same heart-produced sound into an electrical signal which can be transmitted to peripheral recording or reproducing equipment. In the embodiment shown in FIGS. 1–5, the sound converting means is an electronic transducer 10.

Transducer 10 consists of an electronic amplifier housed in an enclosure 19. Enclosure 19 attaches to the stethoscope valve body 33 by means of a coupler fitting 13. Coupler fitting 13 consists of a coupler stem 13b which screws into a threaded opening 37 in valve body 33. A nut 13a turns on stem 13b to tighten the enclosure 19 onto valve body 33. This allows transducer 10 to be easily attached or removed from valve body 33 by means of coupler fitting 13. This easy attachment method allows the transducer 10 to be applied to any one of a number of stethoscopes which have a suitable threaded fitting 37. Thus, the transducer 10 could be kept in one location near the recording equipment and affixed to the stethoscope of any person wishing to examine a patient in conjunction with the recording apparatus. It should be noted that other means of attaching the transducer 10 to stethoscope 30 different from the coupler fitting 13 may also be utilized. Other suitable means of attachment and other locations for attachment on stethoscope 30 may also be used.

When transducer 10 is attached to valve body 33, valve bore 55 is alined with transducer bore 28. This provides an air column for the transmission of the acoustical wave from either diaphragm pickup 32 or bell pickup 31 directly into transducer 10. When the acoustical wave enters transducer 10, it is picked up by a microphone 21 which converts the acoustical wave to an electrical signal in a manner well known in the art. (See FIGS. 4 and 5). The output of microphone 21 is transmitted into an amplifier circuit which is shown in FIG. 5 and will be described in detail later. The microphone 21 is held in place in enclosure 19 by means of a nylon microphone support 22 and a nylon top bracket 24. Screws 26 extend through nylon top bracket 24 and spacers 25 into support 22. O-Ring 23 and rubber gasket 27 are utilized to seal microphone 21 in place in enclosure 19. Microphone assembly 20 produces signals which are amplified approximately 1000 fold by the amplifier circuit shown in FIG. 5. The electrical signals produced by amplifier circuit 40 are transmitted to output terminal 12 shown schematically in FIG. 5 and shown as jack 12 in FIGS. 2 and 3.

The amplifier control circuit of the preferred embodiment is illustrated in FIG. 5. Referring to FIG. 5, a microphone 21 (positioned within the housing 19 to receive the acoustical wave) has a first signal output 21a and a reference output 21b. The reference output 21b of the microphone 21 is directly connected to the common reference terminal 46. The signal output 21a of the microphone 21 is connected by means of a resistor 43 to a non-inverting (+) input of an operational amplifier 44. The amplifier 44 in the preferred embodiment is of the uA 741 type, well known in the art. The amplifier 741 further has an inverting (−) input, a signal output 44a, a supply input 44b and a reference stabilizer input 44c. The signal output 44a of the operational amplifier 44 is directly connected to the negative output jack 12 (−) and is also connected by means of a resistor 41 to the inverting (−) input of the amplifier 44. The inverting (−) input of the amplifier 44 is also connected by means of a resistor 45 to the common bus 46. The supply terminal 44b of the amplifier 44 is connected to the negative terminal of a battery 18. In the preferred embodiment, the battery 18 is a 9 volt battery, also having a positive terminal directly connected to movable contact of a switch 11. The switch 11 also has a stationary contact directly connected to the reference input terminal 44c of the amplifier 44. The positive terminal of the battery 18 is also connected by means of a resistor 42 to the common bus 46. The common bus 46 is directly connected to the positive output jack 12(+). It will be noted that in the preferred embodiment, the common reference is of positive potential.

In the preferred embodiment, the values of the resistors 41, 42, 43 and 45 are as follows:

| Resistor | Value (Ohms) |
|----------|--------------|
| 41 | 100,000 ± 5% |
| 42 | 2,200 ± 5% |
| 43 | 100 ± 10% |
| 45 | 110 ± 1% |

The switch 11 shown schematically in FIG. 5 is of the momentary-contact type which allows the stethoscope user to turn on the power to stethoscope 10 by merely holding down the push button for the switch 11. In this way, the user of transducer equipped stethoscope 1 can utilize the stethoscope as a mechanical stethoscope and switch in the transducer 10 at will to provide an electrical signal for recording or transmission. It should be noted that various other suitable sound conversion devices could be used in place of the microphone assembly 20, such as a piezoelectric crystal. In addition, it is not necessary that the amplifier shown in FIG. 5 be utilized in the form shown. Also, by utilizing printed circuit boards, electronic chips and miniature batteries, the physical size of transducer 10 could be reduced to a fraction of the size shown in the Figures.

The operation of the transducer equipped stethoscope 1 can be summarized as follows. A stethoscope 30 has a valve body 33 which incorporates a threaded opening 37 for receiving a transducer package 10. By means of a selector valve 36, the stethoscope can be used to monitor the heart sounds of a test subject either through a diaphragm pickup 32 or a bell pickup 31. Either of these pickups is utilized by pressing it against the body of the test subject. The selector valve 36 is turned to the position shown in FIG. 4 when the diaphragm pickup 32 is utilized. If the bell pickup 31 were to be utilized the selector valve 36 would be turned 90° to the left by means of wing nut 36a (see FIG. 2).

The vibration of the test subject's body caused by the heart sounds creates an acoustical wave in either the diaphragm acoustical chamber 53 or the bell acoustical chamber 34. This standing acoustical wave is transmitted through valve bore 55 to the transducer 10 and also through junction element bore 56. As the wave travels through junction element bore 56 into flexible coupling conduit 35 it reaches the user's ears through ear pieces 36. In this way, the stethoscope operator hears the same sounds as he would hear through any conventional mechanical stethoscope.

With transducer 10 attached to stethoscope 30, the acoustical wave produced by either diaphragm pickup 32 or bell pickup 31 impinges on microphone assembly 20. The microphone assembly 20 converts the acoustical wave to an electrical signal which is amplified and transmitted to an output jack terminal 12. The resulting electrical signal can then be transmitted through a cable 16 or other means to a recording instrument 17 such as an oscilloscope, a tape recorder or other reproduction device.

The electrical amplifier is powered by a battery 18. The power from battery 18 is turned on and off by means of a momentary-contact push button switch 11 mounted on the side of the transducer enclosure 19.

The user of the stethoscope 1 merely pushes switch 11 when he wants the sounds he is hearing to be simultaneously transmitted to the recording instruments 17. When switch 11 is activated to switch on power to transducer 10, the user of the stethoscope 1 can still hear the mechanical sounds produced through earpieces 36. Thus, the conversion of the sounds to electrical signals by transducer 10 is accomplished simultaneously with the continued mechanical operation of the stethoscope 30. In this way, the user of the stethoscope 1 can analyze the mechanically produced sounds which he is most accustom to monitoring while at the same time utilizing the transducer 10 to convert the sounds to electrical signals for recording or visual production on an oscilloscope or the like.

It should be noted that the applicant has found through extensive experimentation that very unique acoustical phenomenon occur in the internal conduits of the standard mechanical stethoscope. When attempts are made to attach electrical devices to such mechanical stethoscopes, these acoustical properties are varied. As a result, the applicant has designed his invention to avoid interference with the mechanical sounds produced through ear pieces 36 while at the same time allowing for conversion of the sounds to an electrical signal. This permits the stethoscope user to rely on his trained ear which has become accustomed to "standard" sounds from a mechanical stethoscope while at the same time having an electronical capability for amplifying and recording the same heart sounds which are produced by the stethoscope and converted to an electrical signal by the transducer.

What is claimed is:

1. An improved stethoscope which allows its user to simultaneously monitor heart sounds using his ears while selectively detecting the heart sounds electrically and converting them into a meaningful electrical form for transmission to a receiving station, said improved stethoscope comprising:
    a. mechanical sound pick-up means for producing a confined acoustical wave from a heart pulsation;
    b. said mechanical sound pick-up means including a first acoustical chamber;
    c. a conduit through which an acoustical wave may be transmitted, said conduit being operably communicable with an operator's ears;
    d. a first bore-like passageway, said first passageway being in continuous communication with said first acoustical chamber;
    e. electrical sound conversion means for converting an acoustical wave which may be produced in said acoustical chamber into an electrical signal, said electrical sound conversion means including:
       i. housing apparatus;
       ii. means for operably attaching said housing apparatus to the stethoscope;
       iii. a microphone carried by said housing apparatus;
       iv. said housing apparatus containing an acoustical duct;
       v. means for retaining said microphone in sealed communication with said acoustical duct;
       vi. power means for operating said microphone; and
       vii. an out-put terminal carried by said housing apparatus and being in communication with said microphone for distributing an electrical signal which may be produced by said microphone;
    f. means for simultaneously interconnecting said conduit with said first passageway and said acoustical duct to allow heart sounds to be simultaneously transmitted mechanically to a listener's ears and to said microphone.

2. The improved stethoscope of claim 1 wherein said means for simultaneously interconnecting said conduit with said first passageway and said acoustical duct include a second borelike passageway having three openings, one of said three openings communicating with each of said conduit, first passageway and acoustical duct.

3. The improved stethoscope of claim 2 wherein said mechanical sound pick-up means include a second acoustical chamber, and wherein said means for simultaneously interconnecting said conduit with said first passageway and said acoustical duct comprise a selector valve selectively rotatable between a first and a second position, said first position allowing said second bore-like passageway to communicate between said first acoustical chamber, said conduit and said acoustical duct, and said second position allowing said second bore-like passageway to communicate between said second acoustical chamber, said conduit and said acoustical duct.

4. An improved stethoscope for continuously detecting or monitoring heart sounds while selectively and simultaneously detecting the same heart sounds and converting them into a meaningful electrical form for transmission to a receiving station, said improved stethoscope comprising:
    a. means for the mechanical pick-up of heart produced sounds for transmission in the form of an acoustical wave to the ears of the stethoscope user;
    b. an acoustical chamber in communication with said pick-up means for receiving and distributing the acoustical waves;
    c. conduit means containing an air column in continuous communication between said acoustical chamber and earplugs insertable in the operator's ears for transmitting the acoustical wave therethrough;
    d. an electrical transducer attachable to said stethoscope to convert the mechanically produced acoustical wave into an electronic signal, comprising:
       i. a housing;
       ii. a sound duct communicating between said housing and said mechanical sound pick-up means simultaneously with the communication between said mechanical sound pick-up means and said conduit means;
       iii. a microphone contained in said housing and in sealed communication with said sound duct to convert the acoustical wave to an electrical signal;
       iv. power means for operating said mirophone; and
       v. out-put terminal means attached to said housing and in communication with said microphone for distributing the electrical signal produced by said microphone.

5. The improved stethoscope of claim 4 including a solid-state electrical amplifier carried by said housing and interconnected with said mirophone and said power source to amplify the electrical signals produced by said microphone.

6. The improved stethoscope of claim 5 wherein said power means is a battery contained in said housing and further including an electrical switching means connected to said battery for selectively providing power from said battery to said solid-state amplifier.

7. An improved stethoscope for continuously detecting or monitoring heart sounds audibly through earplugs while selectively and simultaneously electrically detecting the same heart sounds and converting them into an electrical form for transmission to receiviing station, said improved stethoscope comprisiing:
   a. a rigid chestpiece body;
   b. means attached to said chestpiece body for the mechanical pick-up of heart produced sounds for transmission in the form of an acoustical wave to the ears of the stethoscope user:
   c. an acoustical chamber within said chestpiece body, said chamber being in communication with said pick-up means for receiving and distributing the acoustical wave;
   d. conduit means containing an air column in continuous communication between said acoustical chamber and the earplugs inserted in the operator's ears for transmitting the acoustical wave therethrough from said acoustical chamber;
   e. electrical sound conversion apparatus attached to said stethoscope to convert the mechanically produced acoustical wave into an electrical signal, comprising:
      i. a housing located adjacent said chestpiece body;
      ii. attachment means interconnecting said chestpiece body and said housing for rigidly attaching said housing to said chestpiece body;
      iii. a sound duct communicating between said housing and said acoustical chamber, said duct having generally parallel walls;
      iv. a sound transducer contained in said housing and in sealed communication with said sound duct to convert the acoustical wave to an electrical signal;
      v. power means for operating said sound transducer; and
      vi. out-put terminal means attached to said housing and communicating with said sound transducer for distributing the electrical signal produced by said sound transducer.

8. The improved stethoscope of claim 7 including a solid-state electrical amplifier carried by said housing and interconnected with said sound transducer and said power source to amplify the electrical signals produced thereby.

9. The improved stethoscope of claim 8 wherein said power means is a battery contained in said housing and further including an electrical switching means connected to said battery for selectively providing power from said battery to said solid-state amplifier.

* * * * *

UNITED STATES PATENT OFFICE
CERTIFICATE OF CORRECTION

PATENT NO. : 3,989,895
DATED : November 2, 1976
INVENTOR(S) : Philip O'Daniel

It is certified that error appears in the above-identified patent and that said Letters Patent are hereby corrected as shown below:

column 1, line 5, delete "1."

column 1, line 9, delete "2."

column 3, line 49 "earpiece" should be --earpieces--.

column 3, line 51 "operator'" should be --operator's--.

column 3, line 68 "is" should be --its--.

column 5, line 63, add --a-- before "movable".

column 7, line 36, add --same-- before "heart".

column 9, line 7, add --a-- before "receiving".

column 9, line 13, delete ":" add --;--.

column 10, line 1, delete "iii" add --ii--.

Signed and Sealed this

First Day of March 1977

[SEAL]

Attest:

RUTH C. MASON
Attesting Officer

C. MARSHALL DANN
Commissioner of Patents and Trademarks